United States Patent
Moszner et al.

(10) Patent No.: US 11,618,799 B2
(45) Date of Patent: Apr. 4, 2023

(54) COMPOSITE WITH REDUCED POLYMERIZATION SHRINKAGE STRESS

(71) Applicant: Ivoclar Vivadent AG, Schaan (LI)

(72) Inventors: Norbert Moszner, Triesen (LI); Yohann Catel, Rans (CH); Iris Lamparth, Grabs (CH)

(73) Assignee: Ivoclar Vivadent AG, Schaan (LI)

( * ) Notice: Subject to any disclaimer, the term of this patent is extended or adjusted under 35 U.S.C. 154(b) by 108 days.

(21) Appl. No.: 17/340,269

(22) Filed: Jun. 7, 2021

(65) Prior Publication Data

US 2022/0002461 A1 Jan. 6, 2022

(30) Foreign Application Priority Data

Jul. 3, 2020 (EP) ................. EP20184024

(51) Int. Cl.

| | | |
|---|---|---|
| *C08F 2/46* | (2006.01) | |
| *C08F 2/50* | (2006.01) | |
| *C08G 61/04* | (2006.01) | |
| *C08F 222/10* | (2006.01) | |
| *C08K 13/02* | (2006.01) | |
| *C08K 3/22* | (2006.01) | |

(52) U.S. Cl.
CPC ........ *C08F 222/1025* (2020.02); *C08K 13/02* (2013.01); *C08K 2003/2244* (2013.01); *C08K 2201/005* (2013.01)

(58) Field of Classification Search
CPC .............. C08K 13/02; C08K 2201/005; C08K 2003/2244; C08F 222/1025; A61K 6/818; A61K 6/833; A61K 6/62; A61K 6/889; C08L 33/10
USPC ........... 522/48, 47, 6, 71, 189, 184, 1; 520/1
See application file for complete search history.

(56) References Cited

U.S. PATENT DOCUMENTS

| | | |
|---|---|---|
| 5,932,675 A | 8/1999 | Rizzardo et al. |
| 6,316,519 B1 | 11/2001 | Berge |
| 2008/0269460 A1 | 10/2008 | Bowman et al. |
| 2012/0016052 A1* | 1/2012 | Bowman .................. C08F 2/38 522/168 |
| 2012/0295228 A1 | 11/2012 | Abuelyaman et al. |

* cited by examiner

*Primary Examiner* — Jessica Whiteley
(74) *Attorney, Agent, or Firm* — Ann M. Knab; Thad McMurray

(57) ABSTRACT

Radically polymerizable dental material which contains at least one compound of Formulae I to III:

Formula I

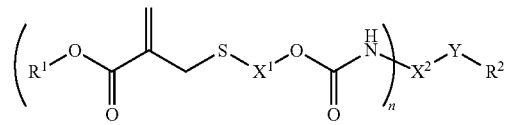

Formula II

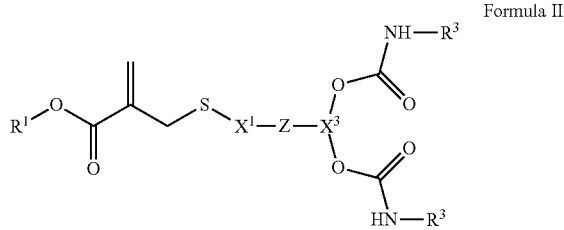

Formula III

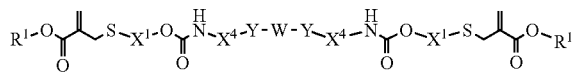

The material preferably additionally contains a radically polymerizable monomer, an initiator for the radical polymerization and filler. It is characterized in particular by a low polymerization contraction stress.

22 Claims, No Drawings

COMPOSITE WITH REDUCED POLYMERIZATION SHRINKAGE STRESS

CROSS-REFERENCE TO RELATED APPLICATIONS

This application claims priority to European patent application No. 20184024.6 filed on Jul. 3, 2020, the disclosure of which is incorporated herein by reference in its entirety.

TECHNICAL FIELD

The present invention relates to thermally and/or light-curing composites for the preparation of dental cements and filling composites, artificial teeth, inlays, onlays, crowns, bridges or veneering materials.

BACKGROUND

Dental composites which are used e.g. as composite cement or as direct filling material, inlay, onlay, crown or veneering material contain a polymerizable organic matrix and one or more fillers, which are usually surface-modified with a polymerizable bonding agent. Depending on the type of the fillers, the monomer matrix and the application the filling level can vary between approx. 50 and 90 wt.-%, wherein cements have a lower filling level compared with filling composites.

As a rule, the polymerizable organic matrix contains a mixture of monomers, initiator components, stabilizers and pigments. Mixtures of dimethacrylates are usually used as resins. Examples of these are the high-viscosity dimethacrylates 2,2-bis[4-(2-hydroxy-3-methacryloyloxypropyl)phenyl]propane (bis-GMA) and 1,6-bis-[2-methacryloyloxyethoxycarbonylamino]-2,4,4-trimethylhexane (UDMA) or the low-viscosity dimethacrylates, used as diluting monomers, such as e.g. bismethacryloyloxymethyltricyclo[5.2.1.]decane (TCDMA), decanediol-1,10-dimethacrylate ($D_3MA$) and triethylene glycol dimethacrylate (TEGDMA).

In the radical polymerization of dental composites volume contraction occurs due to the polymerization shrinkage ($\Delta V_P$) of the monomers used, which can lead to a very disadvantageous formation of marginal gaps in the case of filling composites. During the polymerization of monofunctional methacrylates, such as e.g. MMA ($\Delta V_P$=21.0 vol.-%), this polymerization shrinkage does not lead to the build-up of a polymerization shrinkage stress (PSS) because the reduction in volume can be compensated for by flow of the macromolecules formed. In the case of the crosslinking polymerization of multifunctional methacrylates, however, a three-dimensional polymer network already forms within a few seconds at the so-called gel point, i.e. already at low monomer conversion, with the result that the polymerization shrinkage can no longer be compensated for by viscous flow and a considerable PSS builds up in the material as the monomer conversion increases. The development of the PSS in filling composites is dependent on numerous factors, including the extent of the volume contraction during polymerization (curing or post-curing), the viscoelastic properties (modulus of elasticity and modular organization, glass transition temperature ($T_G$) of monomer and polymer, viscosity and flow behaviour), the polymerization kinetics of the polymer network formation (resin functionality, crosslinking density, proportion of cyclic structures, polymerization rate, temperature, monomer and double-bond conversion), the type of curing and the type of restoration (layer thickness, cavity geometry). A particularly high PSS is observed in the case of light curing (cf. R. R. Braga, R. Y. Ballester, J. L. Ferracane, Dent. Mater. 21 (2005) 962-970; J. W. Stansbury, Dent. Mater. 28 (2012) 13-22).

Numerous strategies have been pursued to reduce the PSS. This applies to clinical methods, such as e.g. the incremental layer technique, the use of cavity varnishes with low modulus of elasticity to form a stress-absorbing layer, the use of special exposure strategies (soft-start) or the preheating of the composite to improve the flow properties. The use of novel low-shrinkage monomers, e.g. of monomers with ring-opening polymerizable groups, or the use of tailored crosslinking agents, e.g. with photo- or thermolabile spacers, can likewise lead to composites with low PSS.

In addition, it has been attempted to reduce the PSS through the addition of hyperbranched monomers, nanogels or nanotubes as well as low-profile additives or expandable fillers.

WO 98/37104 and corresponding U.S. Pat. No. 6,316,519B1, which U.S. patent is hereby incorporated by reference, discloses a process for controlling the molecular weight in the preparation of linear polymers by photoinitiated radical polymerization of vinyl monomers, in which the photoinitiator is used together with an addition-fragmentation chain transfer reagent.

According to WO 2006/086646 A2 and corresponding US 20080269460A1 and US 20120016052A1, which U.S. patent applications are hereby incorporated by reference, the PSS in crosslinked polymers is able to be reduced through the incorporation of groups which enable a reversible chain cleavage into the polymer network. After the curing, these groups are activated for example by irradiating with light. This is intended to bring about a reversible cleavage of the polymer chains, through which the PSS is relieved. Reversible Addition-Fragmentation chain Transfer agents (RAFT), such as e.g. allyl sulfides, dithiocarbamates and thiocarbonates, are used for the incorporation of these groups into the polymer chains. Such RAFT reagents are known from controlled radical polymerization (cf. e.g. Moad, G.; Rizzardo, E.; Thang, S. H. Polymer 2008, 49, 1079-1131).

US 20120295228 A1, which is hereby incorporated by reference, discloses radically polymerizable dental materials which contain ethylenically unsaturated monomers with allyl disulfide groups, which are active as addition-fragmentation materials and are intended to reduce the PSS.

In addition, it is known that mercaptans, such as e.g. mercaptobenzene, benzyl mercaptan, mercaptopropionic acid methyl ester, 1,6-hexanedithiol or trimethylolpropane tris-(3-mercaptopropionate), lead to a significant reduction in polymer chain length and to the formation of networks that are more homogeneous and have lower $T_G$ values and narrower distribution (Hacioglu, B.; Berchtold, K. A.; Lovell, L. G.; Nie, J.; Bowman, C. N. Biomaterials 2002, 23, 4057-4067; Dean, K. M.; Cook, W. D.; Lin, M. Y. Eur. Polym. J. 2006, 42, 2872-2887).

U.S. Pat. No. 5,932,675, which is hereby incorporated by reference, discloses a process for the preparation of polymers with low molecular weight by radical polymerization. The molecular weight is controlled through the addition of chain transfer reagents such as e.g. α-(t-butanethiomethyl) styrene.

A disadvantage of the known processes is that the addition of transfer-active compounds usually leads to a significant reduction in the polymerization rate, above all in the case of sulfur compounds. In addition, for dental applications, in practice the use of mercaptans is ruled out due to their odour and the use of many other RAFT reagents is ruled out due to their colour.

SUMMARY

The object of the invention is to provide polymerizable dental materials which do not have the disadvantages named above and which are characterized, compared with the state of the art, by a reduced polymerization shrinkage stress (PSS) with comparable mechanical properties and comparable polymerization rate. In addition, the materials are to have a more homogeneous network architecture and a narrower range for the glass transition temperature. Moreover, they are to have an odour that is acceptable for intraoral application and no intrinsic colour.

DETAILED DESCRIPTION

The object is achieved according to the invention by compositions which contain at least one compound of Formulae I to III:

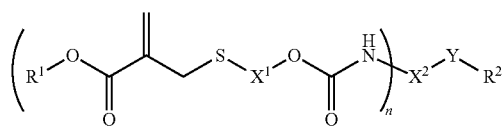

Formula I

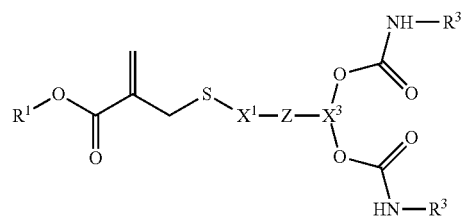

Formula II

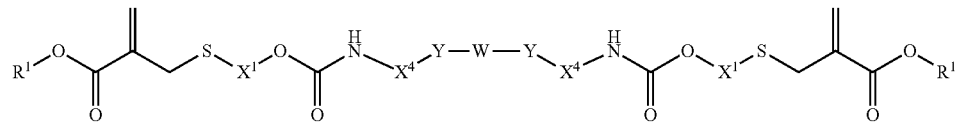

Formula III

Herein the meanings are as follows:

$R^1$ hydrogen, an aliphatic linear or branched $C_1$-$C_{15}$ alkyl radical, which can be interrupted by one or more, preferably 1 to 3, O or S and which can be substituted or unsubstituted, benzyl or phenyl;

$R^2$ hydrogen, an aliphatic linear or branched $C_1$-$C_{15}$ alkyl radical, which can be interrupted by one or more, preferably 1 to 3, O or S and which can be substituted or unsubstituted, benzyl, an aromatic $C_6$-$C_{18}$ radical, which can be substituted or unsubstituted, or a (meth)acryloyloxy group;

$R^3$ an aliphatic linear or branched $C_1$-$C_{15}$ alkyl radical, which can be interrupted by one or more, preferably 1 to 3, O and which can be substituted or unsubstituted, benzyl, or an aromatic $C_6$-$C_{18}$ radical, which can be substituted or unsubstituted;

$X^1$ a linear or branched aliphatic $C_1$-$C_{15}$ alkylene radical, which can be interrupted by one or more, preferably 1 to 3, O or S, or a cycloaliphatic $C_6$-$C_{16}$ radical;

$X^2$ an (n+1)-valent organic $C_1$-$C_{20}$ radical, preferably an aliphatic $C_1$-$C_{20}$ radical, which can be interrupted by one or more, preferably 1 to 3, O or S, a cycloaliphatic $C_5$-$C_{20}$ radical, an aromatic $C_6$-$C_{20}$ radical or an isocyanuric acid radical according to the following formula:

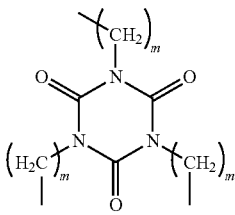

$X^3$ a 3-valent linear or branched aliphatic $C_3$-$C_{20}$ radical;

$X^4$ a 2-valent organic $C_2$-$C_{30}$ radical, preferably an aliphatic $C_2$-$C_{20}$ radical, a cycloaliphatic $C_5$-$C_{20}$ radical, an aromatic $C_6$-$C_{20}$ radical or combinations thereof, wherein these radicals can in each case be substituted by one or more, preferably 1 to 3, methyl groups or are unsubstituted;

Y is absent or an ether (—O—), ester (—COO— or —OOC—), urethane (—NR$^4$—CO—O— or —O—CO—NR$^4$—) or amide group (—CONR$^4$— or —NR$^4$—CO—), wherein $R^4$ in each case represents H or a $C_1$-$C_3$ alkyl radical;

Z is absent or an ether (—O—), ester (—COO— or —OOC—), or amide group (—CONR$^5$— or —NR$^5$—CO—), wherein $R^5$ represents H or a $C_1$-$C_3$ alkyl radical;

W an oligomeric polyester, polyether or polythioether group;

m 1, 2, 3, 4, 5 or preferably 6;

n 1, 2, 3 or 4, wherein, if $X^2$ is an isocyanuric acid radical, then Y and $R^2$ are absent and n is 3.

W preferably has a molar mass of 500-3000 g/mol. The molar mass of W is determined on the basis of the oligomeric building blocks used in the synthesis, e.g. the OH-telechelic polyether or polyester. For example, OH-telechelic PEG 1000 available for sale contains approx. 22 (HO—(CH$_2$—CH$_2$—O—)$_{22}$H) repeating units with a molar mass of in each case 44 g/mol. Together with the terminal OH group and the terminal H atom, a molar weight of 985 g/mol results. The molar mass of the oligomers used for the synthesis is preferably determined by means of vapour pressure osmometry, ebullioscopy or cryoscopy. It is the number-average, absolute molar mass.

Preferred polyether groups are oligomers of ethylene or propylene glycol building blocks or ring-opening homo- or copolymers made of ethylene oxide, propylene oxide and/or tetrahydrofuran. Preferred polyester groups are condensation polymers made of aliphatic $C_2$-$C_{10}$ diols and $C_3$-$C_{10}$ dicarboxylic acids or $C_3$-$C_8$-α,ω-hydroxycarboxylic acids as well as ring-opening polymers from caprolactone. Preferred polythioether groups are condensation polymers from α,ω-dihalogen-$C_2$-$C_{10}$-alkanes with sodium sulfide with a maximum of five sulfur atoms in the building block, wherein in all cases the compounds according to the invention of Formulae I to III preferably contain in each case no more than five sulfur atoms per molecule.

Preferred halogens are chlorine or bromine. The substituents optionally present in the case of the individual radicals are preferably selected in each case from $C_1$-$C_3$ alkyl groups, in particular $CH_3$— and/or $C_2H_5$—, halogen, —OH, —$OCH_3$ or —O—$COCH_3$, polymerizable vinyl, (meth)acryloyloxy and/or (meth)acrylamide groups. The radicals can be substituted in each case with one or with several substituents. The radicals are preferably substituted with 1 to 3 substituents or unsubstituted, wherein in particular aliphatic radicals are preferably not substituted.

All stereoisomeric forms as well as mixtures of different stereoisomeric forms, such as e.g. racemates, are covered by Formulae I, II and III and all other formulae shown herein. The formulae extend only to those compounds which are compatible with the theory of chemical valence. The indication that a radical is interrupted e.g. by one or more O or S atoms is to be understood to mean that these groups are inserted into the carbon chain of the radical. These groups are thus bordered on both sides by C atoms and cannot be terminal. $C_1$ radicals cannot, for example, be interrupted, branched, cyclic or aromatic. Corresponding to the usual nomenclature, by aromatic hydrocarbon radicals is also meant those radicals which contain aromatic and non-aromatic groups.

The compounds of Formulae I to III are characterized in that they contain at least one allyl sulfide group of the formula $R^1$—O—CO—C(=$CH_2$)—$CH_2$—S—$X^1$— and at least one urethane group, wherein the number of urethane groups preferably corresponds to the number of allyl sulfide groups or is greater. The ratio of allyl sulfide groups to urethane groups is preferably 1:1 to 1:2. Compounds of Formulae I to III are also referred to as urethane allyl sulfides or allyl sulfides herein.

The variables preferably have the following meanings:
$R^1$ hydrogen, an aliphatic linear or branched $C_1$-$C_{10}$ alkyl radical, which can be interrupted by one or more, preferably 1 to 2, O and which can carry one or more, preferably 1 to 3, substituents, which are preferably selected from —$CH_3$, —$C_2H_5$ and/or polymerizable (meth)acryloyloxy groups, or is unsubstituted, benzyl or phenyl;
$R^2$ hydrogen, an aliphatic linear or branched $C_1$-$C_{10}$ alkyl radical, which can be interrupted by one or more, preferably 1 to 2, O and which can carry one or more, preferably 1 to 3, substituents, which are preferably selected from —$CH_3$, —$C_2H_5$ and/or polymerizable (meth)acryloyloxy groups, or is unsubstituted, benzyl, or an aromatic $C_6$-$C_{12}$ radical, which can carry one or more, preferably 1 to 3, substituents, which are preferably selected from —$CH_3$, —$C_2H_5$, and/or polymerizable (meth)acryloyloxy groups, or is unsubstituted, or a (meth) acryloyloxy group;
$R^3$ an aliphatic linear or branched $C_1$-$C_{10}$ alkyl radical, which can carry one or more, preferably 1 to 3, substituents, which are preferably selected from —$CH_3$, —$C_2H_5$, halogen and/or polymerizable (meth)acryloyloxy groups, or is unsubstituted, benzyl, or an aromatic $C_6$-$C_{18}$ radical, which can carry one or more, preferably 1 to 3, substituents, which are preferably selected from —$CH_3$, —$C_2H_5$, polymerizable vinyl and/or (meth)acryloyloxy groups, or is unsubstituted;
$X^1$ a linear or branched aliphatic $C_1$-$C_{10}$ alkylene radical, which can be interrupted by one or more, preferably 1 to 2, O, or a cycloaliphatic $C_6$-$C_{12}$ radical;
$X^2$ an (n+1)-valent organic $C_1$-$C_{15}$ radical, preferably an aliphatic $C_1$-$C_{15}$ radical, which can be interrupted by one or more, preferably 1 to 2, O, a cycloaliphatic $C_5$-$C_{10}$ radical or an aromatic $C_6$-$C_{14}$ radical;
$X^3$ a 3-valent linear or branched aliphatic $C_3$-$C_{10}$ radical;
$X^4$ a 2-valent organic $C_2$-$C_{20}$ radical, preferably an aliphatic $C_2$-$C_{20}$ radical, a cycloaliphatic $C_5$-$C_{10}$ radical, which can carry one or more, preferably 1 to 2, methyl groups as substituents or is unsubstituted, or a combination thereof;
Y is absent or an ester or urethane group;
Z is absent or an ether or ester group;
W an oligomeric polyester or polyether group and
n 1, 2 or 3.

The variables particularly preferably have the following meanings:
$R^1$ an aliphatic linear or branched $C_1$-$C_4$ alkyl radical or benzyl (Ph-$CH_2$—), quite particularly preferably methyl or ethyl;
$R^2$ hydrogen or a (meth)acryloyloxy group;
$R^3$ a linear $C_1$-$C_3$ alkyl radical, benzyl (Ph-$CH_2$—), phenyl (Ph-) or p-tolyl ($H_3$C-Ph-), wherein these radicals can be substituted in each case by a (meth)acryloyloxy group;
$X^1$ a linear $C_1$-$C_3$ alkylene radical;
$X^2$ an (n+1)-valent linear or branched aliphatic $C_2$-$C_{12}$ radical, which can be interrupted by 1 to 3O, or an aromatic $C_6$-$C_{12}$ radical;
$X^3$ a 3-valent linear or branched aliphatic $C_3$-$C_4$ radical; in particular —$CH_2$—CH (-)—$CH_2$—;
$X^4$ a 2-valent aliphatic $C_2$-$C_{10}$ radical or a cycloaliphatic $C_6$ radical, which can be substituted with 1 to 3 methyl groups;
Y is absent or an ester or urethane group;
Z is absent;
W an oligomeric polyester or polyether group and
n 1, 2 or 3, in particular 1 or 2.

Compounds of Formula I are quite particularly preferred, and compounds of Formula I in which the variables have the following meanings are most preferred:
$R^1$ a linear or branched $C_1$-$C_3$ alkyl radical or benzyl (Ph-$CH_2$—), quite particularly preferably methyl or ethyl;
$R^2$ hydrogen or a (meth)acryloyloxy group;
$X^1$ a linear $C_1$-$C_3$ alkylene radical;
$X^2$ an (n+1)-valent linear aliphatic $C_2$-$C_{12}$ radical, which can be substituted by 1 to 3 methyl groups and which can be interrupted by 1 to 3O, or an aromatic $C_6$-$C_{12}$ radical, which can be substituted by 1 to 4 methyl groups, wherein the aromatic $C_6$-$C_{12}$ radical is preferably selected from -Ph-, —$CH_2$-Ph-, —$CH_2$-Ph-$CH_2$— and —C($CH_3$)$_2$-Ph-C($CH_3$)$_2$—;
Y is absent or —O—;
n 1 or 2.

Polymerization transfer-active compounds of Formulae I to III are not known and can be prepared using known synthesis methods. For example, compounds of Formula I can be obtained in two stages. In the first step, through etherification of an α-chloromethyl acrylate with an α,ω-hydroxyalkylmercaptan, an OH-functionalized allyl sulfide is formed, which is then reacted in a second step with a suitable isocyanate to form the urethane allyl sulfide according to the invention of Formula I:
1st Step:
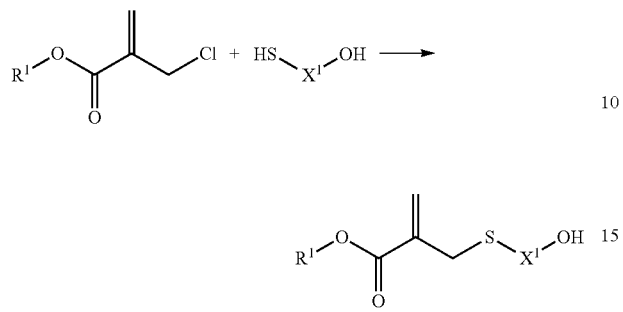
A specific example is:
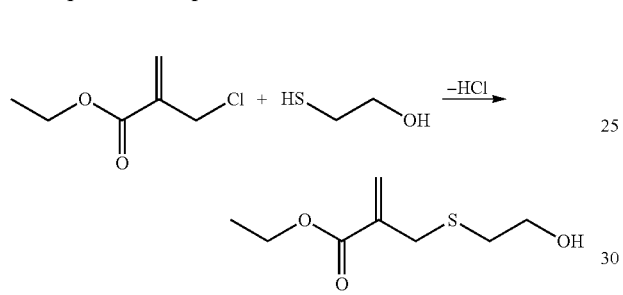
2nd Step:
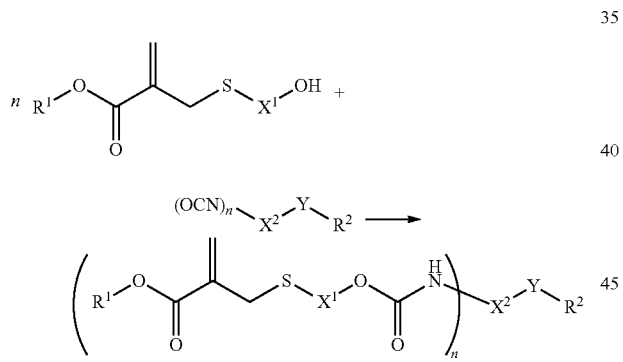
A specific example is:
Analogously, the urethane allyl sulfides according to the invention of Formula II can be prepared in two stages:
1st Step:
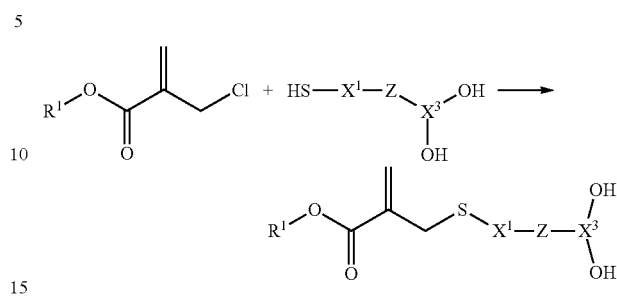
A specific example is:
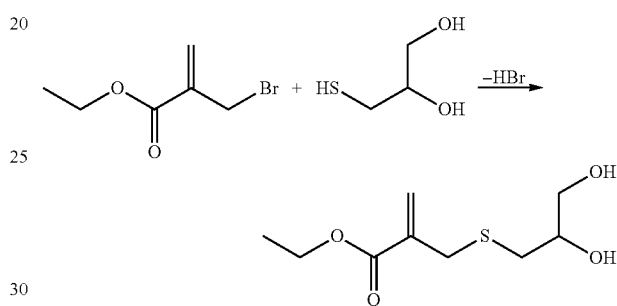
2nd Step:
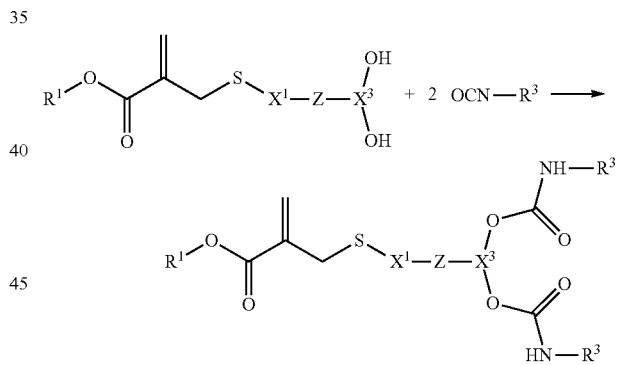
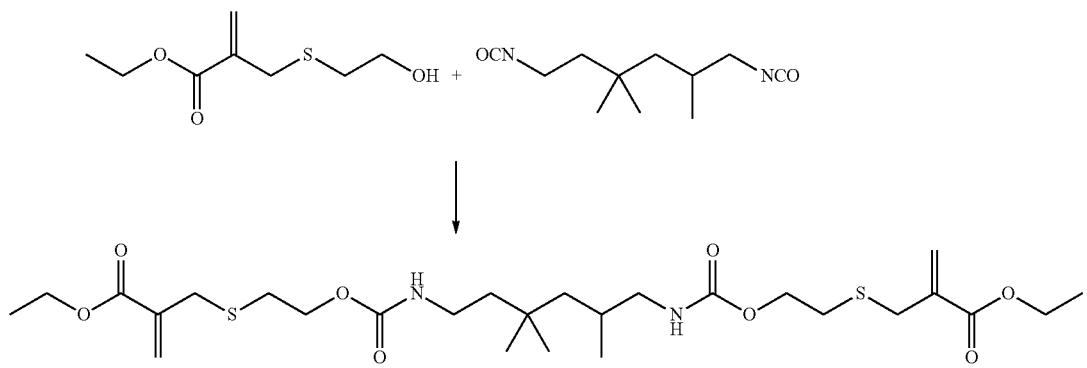

A specific example is:
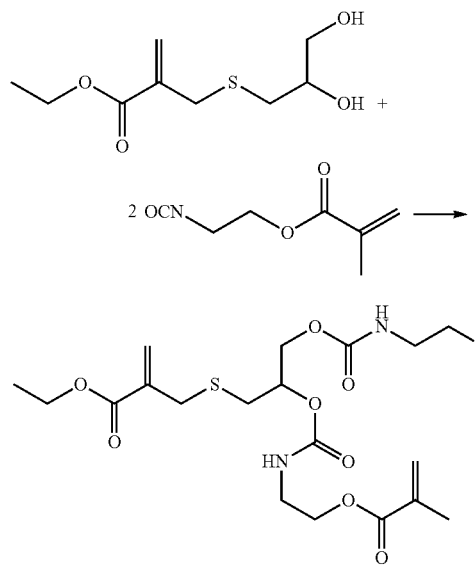
The oligomeric urethane allyl sulfides according to the invention of Formula III can likewise be prepared in two stages (e.g. with Y=urethane):
1st Step:
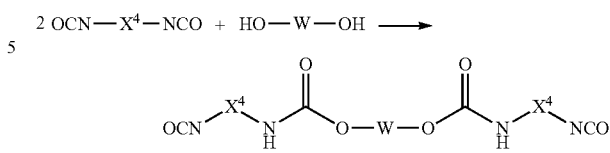
Specific Example:
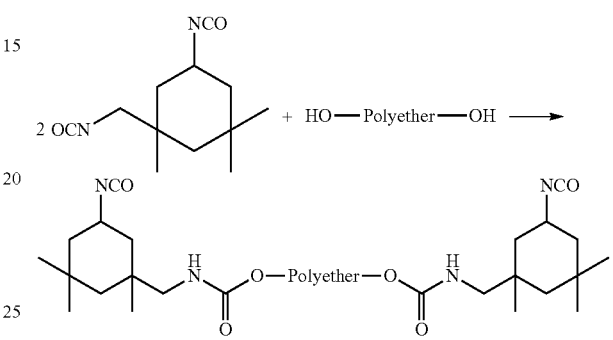
2nd Step:
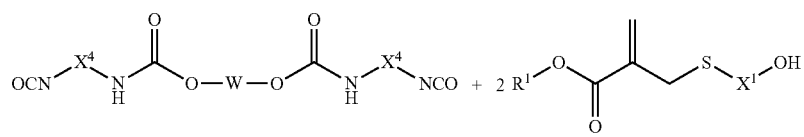
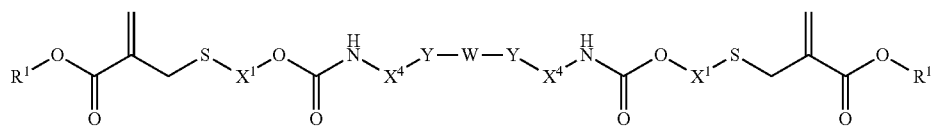
Specific Example:
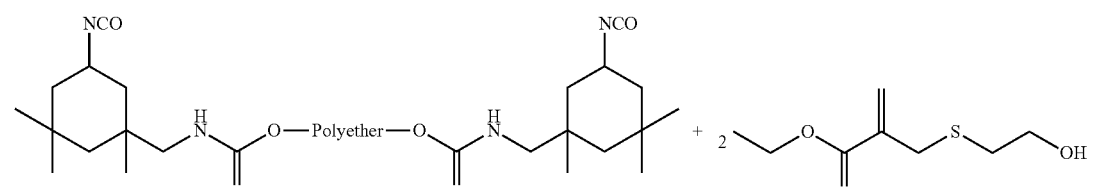

-continued
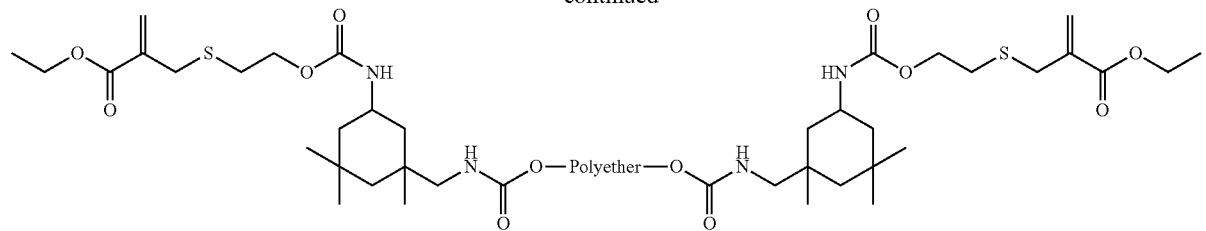
Preferred urethane allyl compounds according to the invention of Formula I are:
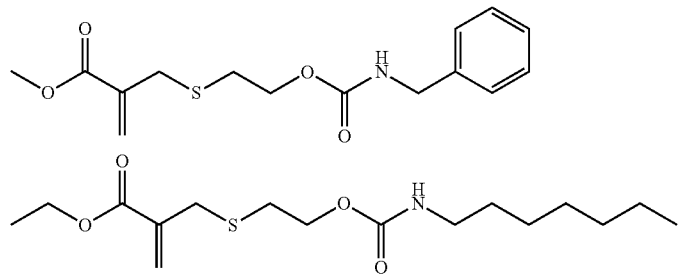
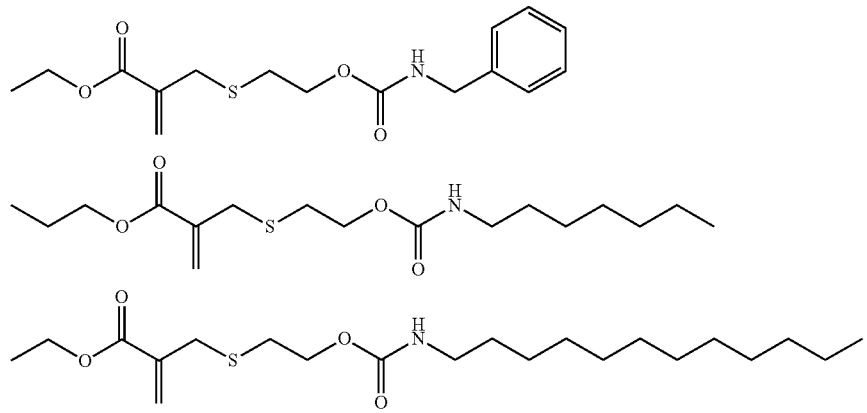
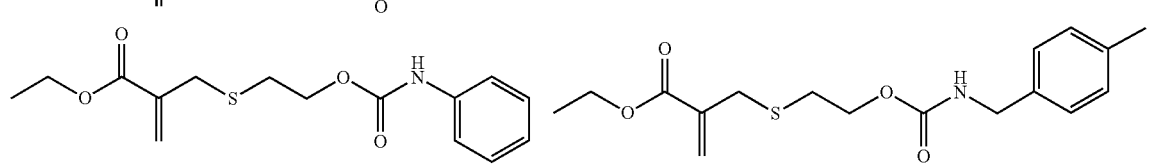
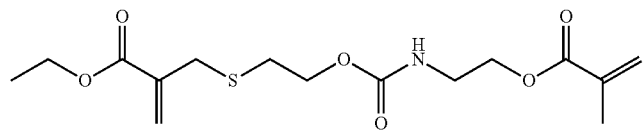
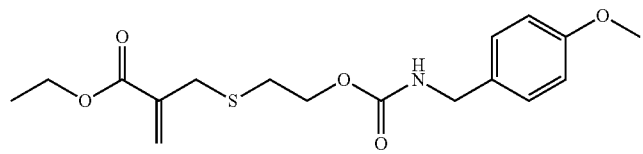

-continued
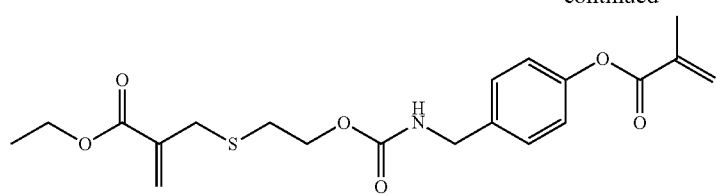
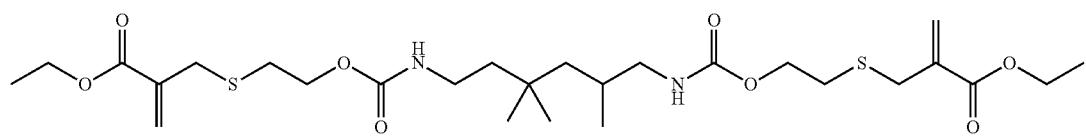
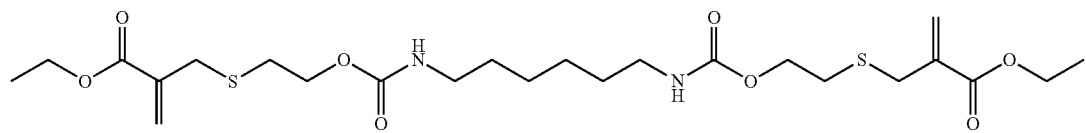
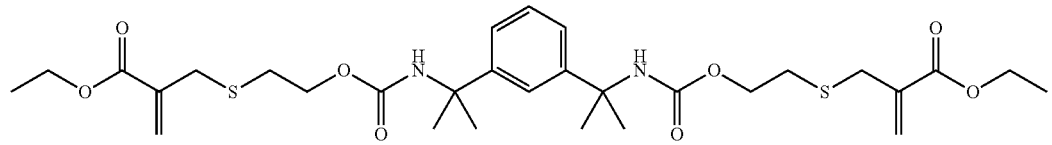
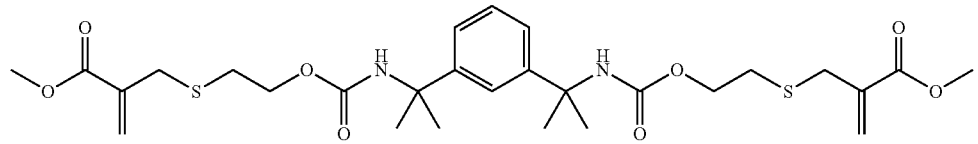
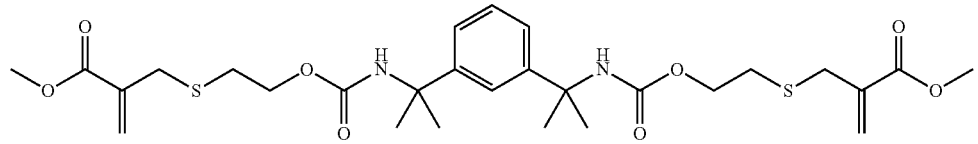
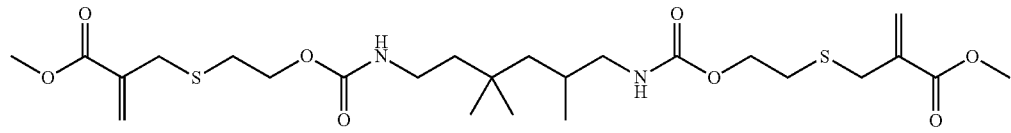
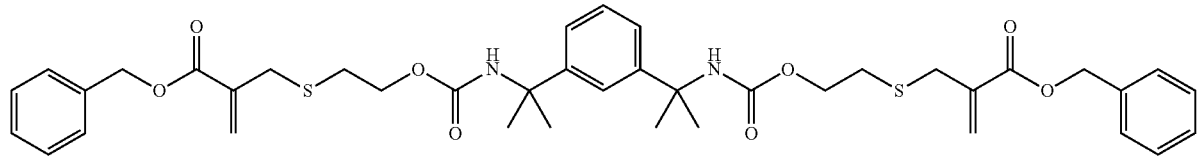
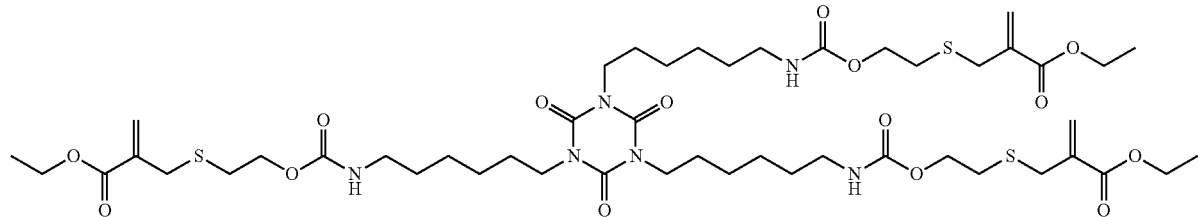

Preferred urethane allyl compounds of Formula II are:
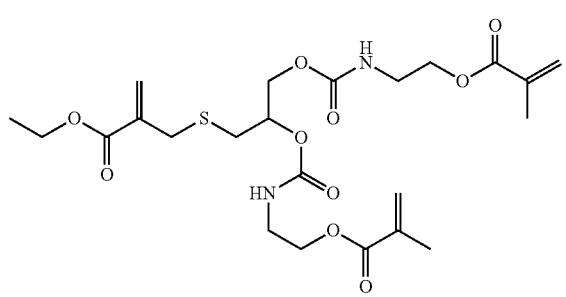
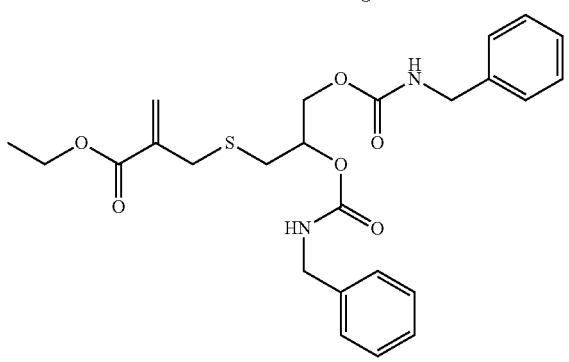
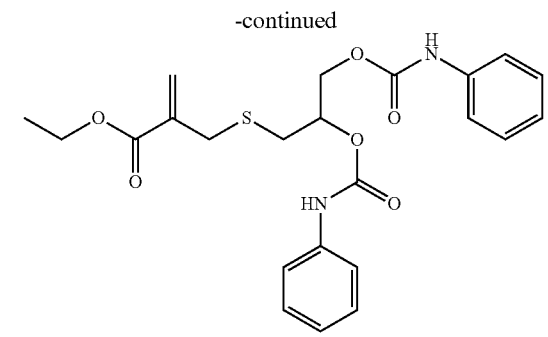
Preferred urethane allyl compounds of Formula III are:
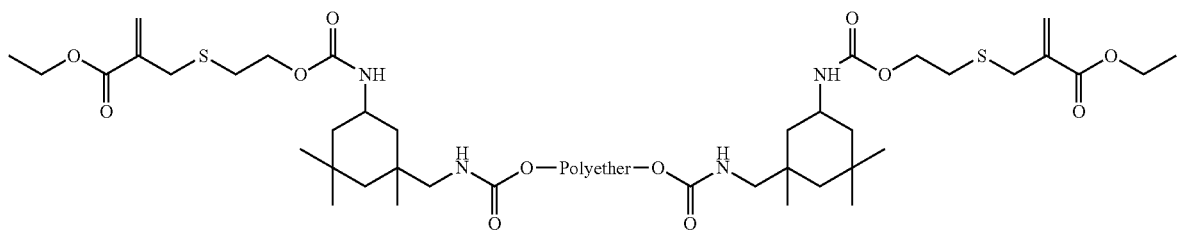
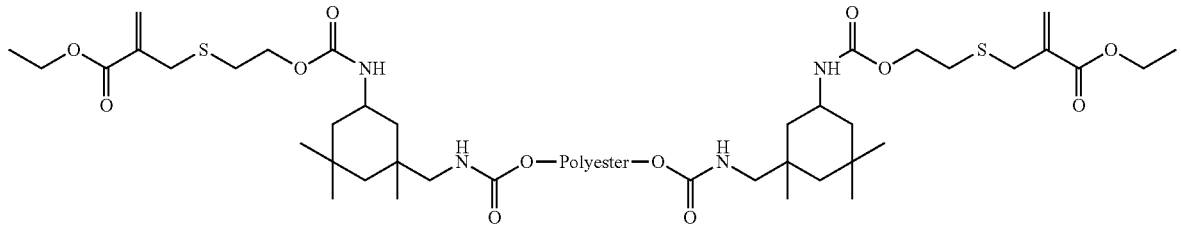
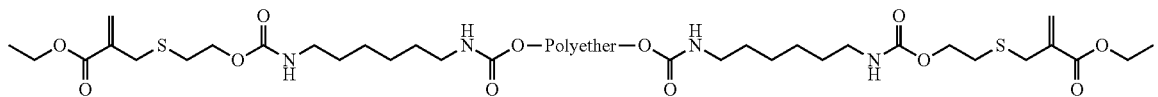
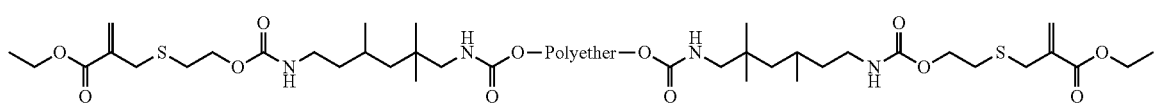

The compounds of Formulae I to III make it possible to control or regulate the network structure during the radical polymerization. They result, surprisingly, in polymer networks that are more homogeneous and have a narrower glass transition, i.e. the glass transition takes place in a narrower temperature range. Accordingly, the PSS is also reduced during the curing of the materials, which is a great advantage for a dental application e.g. as filling material.

In addition to at least one compound of Formula I, II and/or III, the compositions according to the invention preferably contain at least one further radically polymerizable monomer, particularly preferably at least one multifunctional (meth)acrylate or a mixture of mono- and multifunctional (meth)acrylates. By monofunctional (meth)acrylates is meant compounds with one, by multifunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates.

Examples of particularly suitable mono- or multifunctional (meth)acrylates are methyl, ethyl, 2-hydroxyethyl, butyl, benzyl, tetrahydrofurfuryl or isobornyl (meth)acrylate, p-cumyl-phenoxyethylene glycol methacrylate (CMP-1E), bisphenol A di(meth)acrylate, bis-G(M)A (an addition product of (meth)acrylic acid and bisphenol A diglycidyl ether), ethoxylated or propoxylated bisphenol A di(meth)acrylate, such as e.g. bisphenol A dimethacrylate with 3 ethoxy groups (SR-348c, from Sartomer) or 2,2-bis[4-(2-(meth)acryloxypropoxy)phenyl]propane, UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, as well as glycerol di- and tri(meth)acrylate, 1,4-butanediol di(meth)acrylate, 1,10-decanediol di (meth)acrylate ($D_3MA$) or 1,12-dodecanediol di(meth)acrylate.

In addition, thermo- or photolabile di(meth)acrylates, such as e.g. the addition product of 2 mol 2-acetoacetoxyethyl methacrylate and 1 mol 2,2,4-trimethylhexamethylene-1,6-diisocyanate (thermolabile) or methacrylic acid 2-[2-(4-{2-methyl-2-[2-(methacryloyloxy)-ethylcarbamoyloxy]propionyl}-phenoxy)-ethoxycarbonylamino]-ethyl ester, are also suitable. These are suitable in particular for the preparation of materials with debonding-on-demand properties.

In addition to the monomers named above, the dental materials according to the invention can preferably also contain radically polymerizable, acid-group-containing monomers (adhesive monomers). Preferred acid groups are carboxylic acid groups, phosphonic acid groups and phosphoric acid groups. Preferred acid-group-containing monomers are 4-(meth)acryloyl-oxyethyl trimellitic anhydride, 10-methacryloyloxydecylmalonic acid, N-(2-hydroxy-3-methacryloyloxypropyl)-N-phenylglycine and 4-vinylbenzoic acid. Further preferred acid-group-containing monomers are 2-methacryloyloxyethyl phenyl hydrogen phosphate, 10-methacryloyloxydecyl dihydrogen phosphate (MDP) or dipentaerythritolpentamethacryloyloxy phosphate. In addition, 4-vinylbenzylphosphonic acid and 2-[4-(dihydroxyl-phosphoryl)-2-oxabutyl]-acrylic acid are preferred. Amides and esters of the named acid-group-containing monomers, such as e.g. 2-[4-(dihydroxyphosphoryl)-2-oxa-butyl]-acrylic acid-2,4,6-trimethylphenyl ester, and (meth)acrylamide dihydrogen phosphates, such as e.g. 6-methacrylamidohexyl- or 1,3-bis-(methacrylamido)-propan-2-yl dihydrogen phosphate, are further preferred. Adhesive monomers are suitable in particular for the preparation of self-adhesive fixing cements.

For the initiation of the radical polymerization, the compositions according to the invention preferably contain an initiator for the radical polymerization, particularly preferably a photoinitiator. Benzophenone, benzoin and derivatives thereof or α-diketones or derivatives thereof such as 9,10-phenanthrenequinone, 1-phenyl-propane-1,2-dione, diacetyl or 4,4'-dichlorobenzil are suitable in particular as photoinitiators. Preferably camphorquinone (CQ) and 2,2-dimethoxy-2-phenylacetophenone and particularly preferably α-diketones in combination with amines as reducing agent, such as e.g. 4-(dimethylamino)benzoic acid ester (EDMAB), N,N-dimethylaminoethyl methacrylate, N,N-dimethyl-sym.-xylidine or triethanolamine are used. Norrish type I photoinitiators, above all acyl- or bisacylphosphine oxides, are also suitable; and monoacyltrialkyl- or diacyldialkylgermanium compounds, such as e.g. benzoyltrimethylgermanium, dibenzoyldiethylgermanium or bis(4-methoxybenzoyl)diethylgermanium (MBDEGe), are particularly suitable. Mixtures of the different photoinitiators can also be used, such as e.g. bis(4-methoxybenzoyl) diethylgermanium in combination with camphorquinone and 4-dimethylaminobenzoic acid ethyl ester.

According to a preferred embodiment, the dental materials according to the invention additionally contain at least one organic or preferably inorganic filler. Fibrous and in particular particulate fillers are preferred.

Nanofibres, glass fibres, polyamide fibres and carbon fibres are preferred as fibrous fillers. By nanofibres is meant fibres with a length of less than 100 nm. Fibrous fillers are suitable in particular for the preparation of composite materials.

Preferred inorganic fillers are amorphous, spherical, nanoparticulate fillers based on oxides, such as pyrogenic silica or precipitated silica, $ZrO_2$ and $TiO_2$ or mixed oxides of $SiO_2$, $ZrO_2$ and/or $TiO_2$, microfine fillers, such as quartz, glass ceramic or glass powder, and radiopaque fillers, such as ytterbium trifluoride, nanoparticulate tantalum(V) oxide or barium sulfate. The ytterbium trifluoride preferably has a particle size of from 200 to 800 nm.

Preferred glass powders are radiopaque glass powders, in particular of barium or strontium aluminium silicate glasses. Glass powders are obtained by grinding, are purely inorganic in nature and usually consist of splintery parts.

Particulate fillers preferably have a particle size of from 0.01 to 15 µm. Nanoparticulate fillers preferably have a particle size of from 10 to 100 nm and microfine fillers preferably have a particle size of from 0.2 to 5 µm. Unless they are nanoparticulate fillers, radiopaque fillers preferably have a particle size of from 0.2 to 5 µm.

Unless otherwise indicated, all particle sizes are weight-average particle sizes (D50 values), wherein the particle size determination in the range of from 0.1 µm to 1000 µm is preferably effected by means of static light scattering, for example using an LA-960 Static Laser Scattering Particle Size Distribution Analyzer (Horiba, Japan). Here, a laser diode with a wavelength of 655 nm and an LED with a wavelength of 405 nm are used as light sources. The use of two light sources with different wavelengths makes it possible to measure the entire particle size distribution of a specimen in only one measurement pass, wherein the measurement is carried out as a wet measurement. For this purpose, a 0.1 to 0.5% aqueous dispersion of the filler is prepared and the scattered light thereof is measured in a flow cell. The scattered light analysis for calculating particle size and particle-size distribution is effected in accordance with the Mie theory according to DIN/ISO 13320. The measurement of the particle size in the range of from 5 nm to 0.1 μm is preferably effected by dynamic light scattering (DLS) from aqueous particle dispersions, preferably using an He—Ne laser with a wavelength of 633 nm, at a scattering angle of 90° and at 25° C., e.g. using a Malvern Zetasizer Nano ZS (Malvern Instruments, Malvern UK).

Particle sizes smaller than 0.1 μm can also be determined by means of SEM or TEM micrographs. The transmission electron microscopy (TEM) is preferably carried out using a Philips CM30 TEM at an accelerating voltage of 300 kV. For the specimen preparation, drops of the particle dispersion are applied to a 50 Å thick copper grid (mesh size 300 mesh), which is coated with carbon, and then the solvent is evaporated. The particles are counted and the arithmetic mean is calculated.

To improve the bond between the filler particles and the crosslinked polymerization matrix, $SiO_2$-based fillers can be surface-modified with (meth)acrylate-functionalized silanes. An example of such silanes is 3-(meth)acryloyloxypropyl-trimethoxysilane. For the surface-modification of non-silicate fillers, such as e.g. of $ZrO_2$ or $TiO_2$, functionalized acidic phosphates, such as e.g. 10-(meth)acryloyloxydecyl dihydrogen phosphate, can also be used.

The filling level depends on the desired application. Filling composites preferably have a filler content of 75-90 wt.-% and composite cements of 50-75 wt.-%.

In addition to at least one compound of Formula I, II or III, preferred dental materials thus additionally contain at least one radically polymerizable monomer, in particular at least one multifunctional (meth)acrylate or a mixture of mono- and multifunctional (meth)acrylates, at least one initiator for the radical polymerization and preferably also at least one filler.

Optionally, the compositions used according to the invention can contain further additives, above all stabilizers, colorants, microbiocidal active ingredients, fluoride-ion-releasing additives, expanding agents, optical brighteners, plasticizers and/or UV absorbers.

The dental materials according to the invention preferably contain 0.1 to 30 wt.-%, preferably 0.2 to 25 wt.-% and particularly preferably 0.5 to 20 wt.-% of at least one compound of general formula I, II and/or III, preferably I.

Additionally, the materials preferably also contain 0.01 to 5.0 wt.-%, more preferably 0.1 to 5.0 wt.-% and most preferably 0.1 to 3.0 wt.-% initiator(s) for the radical polymerization, particularly preferably a photoinitiator, and preferably also 0 to 99.9 wt.-%, more preferably 10 to 95 wt.-% and most preferably 15 to 95 wt.-% multifunctional (meth)acrylate(s).

Furthermore, the dental materials according to the invention preferably contain 0 to 90 wt.-%, preferably 0 to 85 wt.-% and particularly preferably 0 to 82 wt.-% filler(s), wherein the filler content is matched to the planned use of the materials, as described above.

In addition, the dental materials according to the invention preferably contain 0 to 70 wt.-%, preferably 0.1 to 70 wt.-%, particularly preferably 0.1 to 60 wt.-% other additive(s).

According to the invention, dental materials which contain the following components are particularly preferred:
(a) 0.1 to 30 wt.-%, preferably 0.2 to 25 wt.-% and particularly preferably 0.5 to 20 wt.-% of at least one compound of general formula I, II or III, preferably I,
(b) 10 to 99.1 wt.-%, preferably 10 to 95 wt.-% and particularly preferably 15 to 95 wt.-% of at least one further radically polymerizable monomer, preferably at least one multifunctional (meth)acrylate,
(c) 0.01 to 5.0 wt.-%, preferably 0.1 to 5.0 wt.-% and particularly preferably 0.1 to 3.0 wt.-% of at least one initiator for the radical polymerization,
(d) 0 to 90 wt.-%, preferably 0 to 85 wt.-% and particularly preferably 0 to 82 wt.-% of at least one filler, and
(e) 0 to 70 wt.-%, preferably 0.1 to 70 wt.-% and particularly preferably 0.1 to 60 wt.-% of one or more additives.

Unless otherwise indicated, all quantities relate to the total mass of the materials. The individual quantity ranges can be chosen separately.

Those dental materials which consist of the named components are particularly preferred. Furthermore, those materials in which the individual components are in each case selected from the above-named preferred and particularly preferred substances are preferred. In addition, materials which, in addition to the compound of Formula I, II and/or III, contain no volatile mercaptans, i.e. mercaptans which have a typical mercaptan odour, are particularly preferred. Compositions which contain no further mercaptans and preferably also no other sulfur compounds are quite particularly preferred.

The dental materials according to the invention are suitable in particular as dental cements, filling composites and veneering materials and also as materials for the production of inlays, onlays, crowns and bridges. They have similar mechanical properties (flexural strength and modulus of elasticity) to materials based on dimethacrylates and have a comparable polymerization rate, but are characterized by a reduced polymerization shrinkage stress (PSS), an improved impact resistance and low intrinsic odour.

Compositions which are suitable in particular as dental cements preferably contain:
(a) 0.1 to 20 wt.-%, preferably 0.2 to 15 wt.-% and particularly preferably 0.5 to 10 wt.-% of at least one urethane allyl sulfide of general formula I, II and/or III,
(b) 5 to 50 wt.-%, preferably 10 to 50 wt.-% and particularly preferably 20 to 40 wt.-% of at least one further radically polymerizable monomer,
(c) 0.01 to 5.0 wt.-%, preferably 0.1 to 5.0 wt.-% and particularly preferably 0.2 to 3.0 wt.-% of at least one initiator for the radical polymerization,
(d) 10 to 70 wt.-%, preferably 20 to 70 wt.-% and particularly preferably 30 to 70 wt.-% of at least one filler and
(e) 0 to 5 wt.-%, preferably 0.1 to 5.0 wt.-% and particularly preferably 0.2 to 4.0 wt.-% of one or more additives.

Compositions which are suitable in particular as dental composites preferably contain:
(a) 0.1 to 20 wt.-%, preferably 0.2 to 15 wt.-% and particularly preferably 0.5 to 8 wt.-% of at least one urethane allyl sulfide of general formula I, II and/or III,
(b) 10 to 50 wt.-%, preferably 15 to 40 wt.-% and particularly preferably 15 to 30 wt.-% of at least one further radically polymerizable monomer,
(c) 0.01 to 5.0 wt.-%, preferably 0.1 to 5.0 wt.-% and particularly preferably 0.1 to 0.3 wt.-% of at least one initiator for the radical polymerization,
(d) 10 to 85 wt.-%, preferably 20 to 85 wt.-% and particularly preferably 30 to 85 wt.-% of at least one filler and
(e) 0 to 5 wt.-%, preferably 0.1 to 5.0 wt.-% and particularly preferably 0.2 to 3.0 wt.-% of one or more additives.

The dental materials are suitable primarily for intraoral application by the dentist for the restoration of damaged teeth (therapeutic application), e.g. as dental cements, filling composites and veneering materials. However, they can also be used extraorally, for example in the production or repair of dental restorations, such as inlays, onlays, crowns and bridges (non-therapeutic application).

The invention is explained in more detail in the following with reference to embodiment examples.

EXAMPLES

Example 1

Synthesis of 2-[2-(hydroxyethyl)thiomethyl]acrylic acid ethyl ester (1)

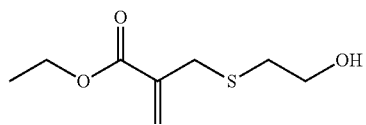

1

A solution of 2-chloromethylacrylic acid ethyl ester (7.43 g, 50.0 mmol) in dichloromethane (50 ml) was added dropwise at 0° C. to a solution of 2-mercaptoethanol (3.91 g, 50.0 mmol) and triethylamine (5.06 g, 50.0 mmol) in dichloromethane (150 ml). The reaction mixture was stirred for 20 h at ambient temperature and then washed with water (2×100 ml) and saturated aqueous sodium chloride solution (3×100 ml), dried over anhydrous sodium sulfate and filtered over silica gel. The filtrate was concentrated on a rotary evaporator and 8.98 g (47.2 mmol; 94%) of a colourless oil was obtained.

$^1$H-NMR (CDCl$_3$, 400 MHz): δ=6.22 (d, 1H; J=1.0 Hz; =C$\underline{H}$), 5.69 (d, 1H; J=1.0 Hz; =C$\underline{H}$), 4.24 (q, 2H; J=7.1 Hz; O—C$\underline{H}_2$), 3.74 (m, 2H; C$\underline{H}_2$OH), 3.43 (s, 2H; C$\underline{H}_2$—S), 2.96 (m, 1H; O$\underline{H}$), 2.68 (t, 2H; J=6.1 Hz; S—C$\underline{H}_2$), 1.32 (t, 3H; J=7.1 Hz; C$\underline{H}_3$).

$^{13}$C-NMR (CDCl$_3$, 100.6 MHz): δ=166.0 (C=O), 136.8 (=C), 126.0 (=CH$_2$), 60.9 (O—CH$_2$), 60.5 (O—CH$_2$), 34.2 (S—CH$_2$), 32.1 (S—CH$_2$), 13.9 (CH$_3$).

Example 2

2-(12-Methyl-6,11-dioxo-5,10-dioxa-2-thia-7-azatridec-12-en-1-yl)acrylic acid ethyl ester (2)

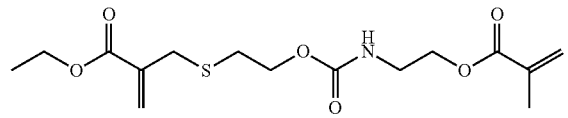

2

2-[2-(Hydroxyethyl)thiomethyl]acrylic acid ethyl ester (60.0 mmol) was dissolved in dichloromethane and dibutyltin dilaurate (10 mg) was added. The isocyanate 2-isocyanatoethyl methacrylate (60.0 mmol) was added dropwise and the reaction mixture was stirred at ambient temperature until an N=C=O band could no longer be detected by means of IR spectroscopy (4 h-24 h). The reaction solution was washed with sodium hydroxide solution (1N), hydrochloric acid (1N) and water, dried over anhydrous sodium sulfate, filtered and concentrated on a rotary evaporator. The crude product was purified by means of column chromatography and the pure compound 2 was obtained as yellowish oil (yield >70%).

$^1$H-NMR (CDCl$_3$, 400 MHz): δ=6.22 (d, 1H; J=0.6 Hz; =C$\underline{H}$), 6.13 (s, 1H; =C$\underline{H}$), 5.69 (s, 1H; =C$\underline{H}$), 5.60 (t, 1H; J=1.5 Hz; =C$\underline{H}$), 5.21 (s, 1H; N$\underline{H}$), 4.27-4.18 (m, 6H; O—C$\underline{H}_2$), 3.52-3.47 (m, 2H; N—C$\underline{H}_2$), 3.42 (s, 2H; C$\underline{H}_2$—S), 2.69 (t, 2H; J=6.7 Hz; S—C$\underline{H}_2$), 1.95 (s, 3H; CH$_3$), 1.32 (t, 3H; J=7.1 Hz; CH$_3$).

$^{13}$C-NMR (CDCl$_3$, 100.6 MHz): δ=167.1 (C=O), 166.0 (C=O), 156.1 (C=O), 136.8 (=C), 135.8 (=C), 126.1 (=CH$_2$), 125.9 (=CH$_2$), 63.5 (O—CH$_2$), 60.9 (O—CH$_2$), 40.0 (N—CH$_2$), 32.6 (S—CH$_2$), 30.0 (S—CH$_2$), 18.2 (CH$_3$), 14.0 (CH$_3$).

Example 3

2-{2-[(Hexylcarbamoyloxy)ethyl]thiomethyl}acrylic acid ethyl ester (3)

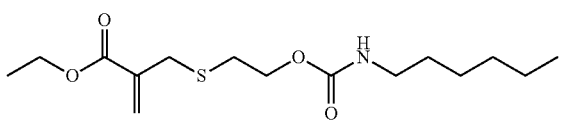

3

Analogously to Example 2, 60 mmol n-hexyl isocyanate was used as isocyanate and 3 was obtained as colourless liquid:

$^1$H-NMR (CDCl$_3$, 400 MHz): δ=6.22 (s, 1H; =C$\underline{H}$), 5.69 (s, 1H; =C$\underline{H}$), 4.81 (s, 1H; N$\underline{H}$), 4.24 (q, 2H; J=7.2 Hz; O—C$\underline{H}_2$), 4.19 (t, 2H; J=6.7 Hz; O—C$\underline{H}_2$), 3.43 (s, 2H; C$\underline{H}_2$—S), 3.16 (m, 2H; N—C$\underline{H}_2$), 2.68 (t, 2H; J=6.7 Hz; S—C$\underline{H}_2$), 1.48 (m, 2H; C$\underline{H}_2$), 1.31 (m, 9H; C$\underline{H}_2$—C$\underline{H}_3$), 0.88 (t, 3H; J=6.7 Hz; C$\underline{H}_3$).

$^{13}$C-NMR (CDCl$_3$, 100.6 MHz): δ=166.0 (C=O), 156.1 (C=O), 136.8 (=C), 126.1 (=CH$_2$), 63.3 (O—CH$_2$), 61.0 (O—CH$_2$), 41.0 (N—CH$_2$), 32.7 (CH$_2$), 31.4 (CH$_2$), 30.2 (CH$_2$), 29.8 (CH$_2$), 26.2 (CH$_2$), 22.5 (CH$_2$), 14.1 (CH$_3$), 13.9 (CH$_3$).

Example 4

2-{2-[(Dodecylcarbamoyloxy)ethyl]thiomethyl}acrylic acid ethyl ester (4)

Analogously to Example 2, 60 mmol dodecyl isocyanate was used as isocyanate and 4 was obtained as colourless liquid:

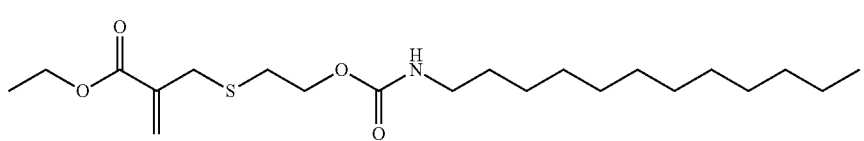

4

¹H-NMR (CDCl₃, 400 MHz): δ=6.22 (d, 1H; J=0.7 Hz; =C$\underline{H}$), 5.69 (s, 1H; =C$\underline{H}$), 4.73 (s, 1H; N$\underline{H}$), 4.24 (q, 2H; J=7.1 Hz; O—C$\underline{H}_2$), 4.19 (t, 2H; J=6.7 Hz; O—C$\underline{H}_2$), 3.43 (s, 2H; C$\underline{H}_2$—S), 3.16 (m, 2H; N—C$\underline{H}_2$), 2.68 (t, 2H; J=6.7 Hz; S—C$\underline{H}_2$), 1.49 (m, 2H; C$\underline{H}_2$), 1.33-1.24 (m, 21H; C$\underline{H}_2$—C$\underline{H}_3$), 0.88 (t, 3H; J=6.8 Hz; C$\underline{H}_3$).

¹³C-NMR (CDCl₃, 100.6 MHz): δ=166.1 (C=O), 156.2 (C=O), 136.9 (=C), 126.1 (=CH₂), 63.3 (O—CH₂), 61.0 (O—CH₂), 41.0 (N—CH₂), 32.7 (CH₂), 31.9 (CH₂), 30.2 (CH₂), 29.9 (CH₂), 29.6 (CH₂), 29.6 (CH₂), 29.5 (CH₂), 29.5 (CH₂), 29.3 (CH₂), 29.2 (CH₂), 26.7 (CH₂), 22.6 (CH₂), 14.1 (CH₃), 14.1 (CH₃).

Example 5

2-{2-[(Benzylcarbamoyloxy)ethyl]thiomethyl}acrylic acid ethyl ester (5)

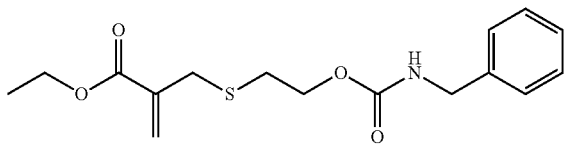

Analogously to Example 2, 60 mmol benzyl isocyanate was used as isocyanate and 5 was obtained as colourless liquid:

¹H-NMR (CDCl₃, 400 MHz): δ=7.35-7.25 (m, 5H; Ar—$\underline{H}$), 6.21 (s, 1H; =C$\underline{H}$), 5.67 (s, 1H; =C$\underline{H}$), 5.23 (s, 1H; N$\underline{H}$), 4.35 (d, 2H; J=6.0 Hz; N—C$\underline{H}_2$), 4.22 (m, 4H; O—C$\underline{H}_2$), 3.41 (s, 2H; C$\underline{H}_2$—S), 2.68 (t, 2H; J=6.8 Hz; S—C$\underline{H}_2$), 1.30 (t, 3H; J=7.2 Hz; C$\underline{H}_3$).

¹³C-NMR (CDCl₃, 100.6 MHz): δ=166.1 (C=O), 156.2 (C=O), 138.3 (Ar—C), 136.8 (=C), 128.6 (Ar—CH), 127.4 (Ar—CH), 126.1 (=CH₂), 63.5 (O—CH₂), 61.0 (O—CH₂), 44.9 (N—CH₂), 32.7 (S—CH₂), 30.1 (S—CH₂), 14.1 (CH₃).

Example 6

11,13,13-Trimethyl-2,23-dimethylene-8,17-dioxo-7,18-dioxa-4,21-dithia-9,16-diazatetracosanedioic acid diethyl ester, isomer mixture (6)

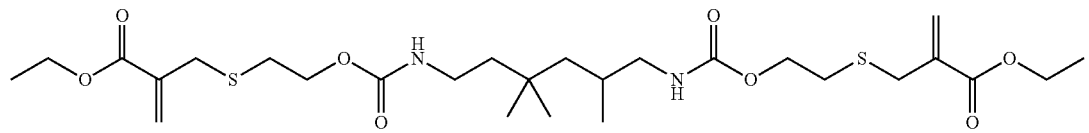

Analogously to Example 2, 30 mmol 2,2,4-trimethylhexamethylene diisocyanate was used as isocyanate and 6 was obtained as colourless solid:

¹H-NMR (CDCl₃, 400 MHz): δ=6.22 (s, 2H; =C$\underline{H}$), 5.69 (s, 2H; =C$\underline{H}$), 5.10-4.71 (m, 2H; N$\underline{H}$), 4.30-4.14 (m, 8H; O—C$\underline{H}_2$), 3.43 (s, 4H; C$\underline{H}_2$—S), 3.23-2.84 (m, 4H; N—C$\underline{H}_2$), 2.68 (t, 4H; J=7.1 Hz; S—C$\underline{H}_2$), 1.64-1.23 (m, 11H, C$\underline{H}$, C$\underline{H}_2$, C$\underline{H}_3$), 0.97-0.85 (m, 9H; C$\underline{H}_3$).

¹³C-NMR (CDCl₃, 100.6 MHz): δ=166.1 (C=O), 156.5 (C=O), 156.4 (C=O), 156.2 (C=O), 156.1 (C=O), 136.9 (=C), 126.1 (=CH₂), 63.4 (O—CH₂), 61.0 (O—CH₂), 51.3 (CH₂), 48.5 (CH₂), 46.4 (CH₂), 45.9 (CH₂), 41.9 (CH₂), 39.3 (CH₂), 39.0 (CH₂), 37.2 (CH₂), 35.0 (CH₂), 32.8 (C), 32.7 (CH₂), 30.2 (CH₂), 29.4 (CH₃), 27.4 (CH₃), 27.4 (CH₃), 26.2 (CH), 25.4 (CH), 25.1 (CH₃), 22.3 (CH₃), 20.5 (CH₃), 14.1 (CH₃).

Example 7

1,3-Bis(2-methyl-10-methylene-4,11-dioxo-5,12-dioxa-8-thia-3-azatetradecan-2-yl)benzene, isomer mixture (7)

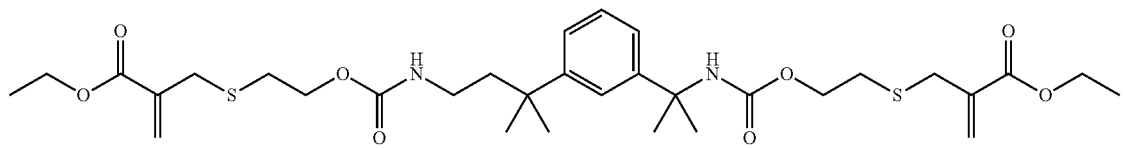

Analogously to Example 2, 30 mmol 1,3-bis(1-isocyanato-1-methylethyl)benzene was used as isocyanate and 7 was obtained as colourless solid:

¹H-NMR (CDCl₃, 400 MHz): δ=7.41 (s, 1H; Ar—$\underline{H}$), 7.32-7.25 (m, 3H; Ar—$\underline{H}$), 6.20 (s, 2H; =C$\underline{H}$), 5.65 (s, 2H; =C$\underline{H}$), 5.21 (s, 2H; N$\underline{H}$), 4.23 (q, 4H; J=7.1 Hz; O—C$\underline{H}_2$), 4.17-4.07 (m, 4H; O—C$\underline{H}_2$), 3.41 (s, 4H; CH₂—S), 2.66 (s, 4H; S—C$\underline{H}_2$), 1.66 (s, 12H; C$\underline{H}_3$), 1.31 (t, 6H; J=7.2 Hz; C$\underline{H}_3$).

¹³C-NMR (CDCl₃, 100.6 MHz): δ=166.0 (C=O), 154.2 (C=O), 146.9 (Ar—C), 136.8 (=C), 128.3 (Ar—CH), 126.1 (=CH₂), 123.2 (Ar—CH), 121.2 (Ar—CH), 62.8 (O—CH₂), 61.0 (O—CH₂), 55.4 (N—C), 32.6 (S—CH₂), 30.2 (S—CH₂), 29.2 (CH₃), 14.1 (CH₃).

Example 8

2-(Dodecylthiomethyl)acrylic acid ethyl ester (8, reference compound)

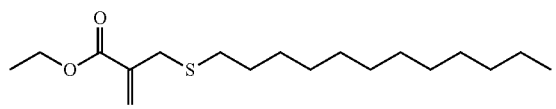

A solution of 2-chloromethylacrylic acid ethyl ester (14.88 g, 0.10 mol) in tetrahydrofuran (50 ml) was added dropwise at 0° C. to a solution of 1-dodecanethiol (20.24 g, 0.10 mol) and triethylamine (10.12 g, 0.10 mol) in tetrahydrofuran (50 ml). The reaction mixture was stirred for 20 h at ambient temperature, then the suspension was filtered. Water (150 ml) and n-heptane (150 ml) were added to the filtrate and the phases were separated. The aqueous phase was extracted with n-heptane (2×150 ml). The combined organic phases were dried over anhydrous sodium sulfate and filtered over silica gel. The filtrate was concentrated on a rotary evaporator and 22.45 g (71.4 mmol; 71%) of a light-yellowish liquid was obtained.

$^1$H-NMR (CDCl$_3$, 400 MHz): δ=6.20 (d, 1H; J=0.9 Hz; =C$\underline{H}$), 5.63 (d, 1H; J=0.9 Hz; =C$\underline{H}$), 4.24 (q, 2H; J=7.1 Hz; O—C$\underline{H}_2$), 3.38 (d, 2H; J=0.6 Hz; C$\underline{H}_2$—S), 2.45 (t, 2H; J=7.5 Hz; S—C$\underline{H}_2$), 1.56 (m, 2H; C$\underline{H}_2$), 1.44-1.16 (m, 24H; C$\underline{H}_2$), 0.88 (t, 3H; J=6.8 Hz; C$\underline{H}_3$).

$^{13}$C-NMR (CDCl$_3$, 100.6 MHz): δ=166.2 (C=O), 137.3 (=C), 125.4 (=CH$_2$), 60.9 (O—CH$_2$), 32.7 (CH$_2$), 31.9 (CH$_2$), 31.6 (CH$_2$), 29.6 (CH$_2$), 29.5 (CH$_2$), 29.3 (CH$_2$), 29.2 (CH$_2$), 28.9 (CH$_2$), 22.6 (CH$_2$), 14.1 (CH$_3$).

Example 9

2-(Methylenepropane-1,3-bis(2-[2-methacryloyloxy-ethylcarbamoyl]ethyl sulfide) (V-783, reference compound)

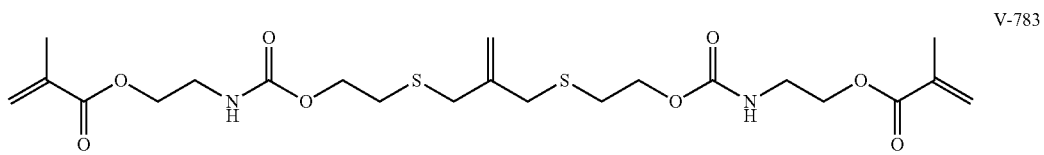 [SMILES: C=C(CSCCOC(=O)NCCOC(=O)C(=C)C)CSCCOC(=O)NCCOC(=O)C(=C)C]

1st Stage: 2-Methylenepropane-1,3-bis(2-hydroxyethyl sulfide)

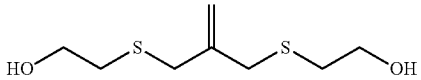

2-Mercaptoethanol (32.03 g; 0.41 mol), 3-chloro-2-chloromethyl-1-propene (25.00 g; 0.20 mol) and 18-Crown-6 (7.95 g; 30.0 mmol) were dissolved in 2-butanone (200 ml). Potassium carbonate (67.72 g; 0.49 mol) was added and the reaction mixture was heated at reflux for 20 h. After cooling, the suspension was diluted with ethyl acetate (200 ml) and filtered over silica gel. The filtrate was concentrated on a rotary evaporator. The crude product was purified by means of column chromatography (SiO$_2$, n-hexane/ethyl acetate) and 32.34 g (0.155 mol; 78%) of a yellowish liquid was obtained.

$^1$H-NMR (CDCl$_3$, 400 MHz): δ=5.04 (s, 2H; =C$\underline{H}$), 3.71 (m, 4H; O—C$\underline{H}_2$), 3.43 (m, 2H; O$\underline{H}$), 3.32 (s, 4H; S—C$\underline{H}_2$), 2.62 (t, 4H; J=6.3 Hz; C$\underline{H}_2$—S).

$^{13}$C-NMR (CDCl$_3$, 100.6 MHz): δ=140.2 (=C), 115.9 (=CH$_2$), 60.2 (O—CH$_2$), 34.7 (S—CH$_2$), 33.4 (CH$_2$—S).

2nd Stage: 2-Methylenepropane-1,3-bis(2-[2-methacryloyloxy-ethylcarbamoyl]ethyl sulfide) (V-783)

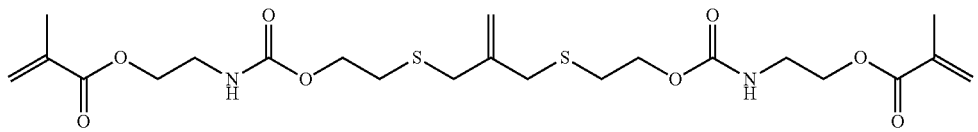 [SMILES: C=C(CSCCOC(=O)NCCOC(=O)C(=C)C)CSCCOC(=O)NCCOC(=O)C(=C)C]

2-Methylenepropane-1,3-bis(2-hydroxyethyl sulfide) of the 1st stage (7.89 g; 37.9 mmol) and dibutyltin dilaurate (0.244 g; 2.0 mmol) were dissolved in acetone (100 ml). Isocyanatoethyl methacrylate (11.75 g; 75.7 mmol) was added and the reaction mixture was stirred at ambient temperature. After 3 h, methanol (20 ml) was added and the solution was concentrated on a rotary evaporator. n-Hexane (100 ml) was added to the residue and the suspension was stirred for 24 h at RT. The suspension was filtered. The filtration residue was washed with n-hexane (100 ml) and dried in a vacuum drying cabinet. 18.57 g (35.8 mmol; 94%) of a white solid was obtained.

$^1$H-NMR (CDCl$_3$, 400 MHz): δ=6.13 (s, 2H; =C$\underline{H}$), 5.60 (m, 2H; =C$\underline{H}$), 5.29 (br s, 2H; N$\underline{H}$), 5.05 (s, 2H; =C$\underline{H}$), 4.25-4.16 (m, 8H; C$\underline{H}_2$—O), 3.50 (m, 4H; C$\underline{H}_2$—N), 3.32 (s, 4H; S—C$\underline{H}_2$), 2.65 (t, 4H; J=6.7 Hz; CH$_2$—S), 1.95 (s, 6H; C$\underline{H}_3$).

$^{13}$C-NMR (CDCl$_3$, 100.6 MHz): δ=167.1 (C=O), 156.0 (C=O), 140.1 (=C), 135.8 (=C), 125.9 (=CH$_2$), 116.3 (=CH$_2$), 63.4 (O—CH$_2$), 63.3 (O—CH$_2$), 40.0 (N—CH$_2$), 35.1 (S—CH$_2$), 29.7 (CH$_2$—S), 18.1 (CH$_3$)

Example 10

Preparation of Filling Composites with Transfer Reagents According to the Invention (Figures in Wt.-%)

A dimethacrylate mixture consisting of 42.19% bis-GMA, 37.57% UDMA and 20.33% D$_3$MA was prepared. The following components were added to 83.85 g of this dimethacrylate mixture: 15 g of the respective allyl sulfide as well as the photoinitiator components CQ (0.15 g), EDMAB (0.4 g) and Lucirin TPO (0.4 g, 2,4,6-trimethylbenzoyldiphenylphosphine oxide).

Using the thus-prepared photopolymerization resin mixture, composites were prepared in a kneader from Linden. For this, the following components were added to 33.63 g photopolymerization resin mixture: 52.21 g of a silanized Ba—Al-borosilicate glass filler (GM27884, from Schott) with an average particle size of 1.0 μm, 4.02 g silanized Ba—Ca—Al-fluorosilicate glass filler (G018-056, from Schott) with an average particle size of 1.0 μm, 4.02 g silanized SiO$_2$—ZrO$_2$ mixed oxide with an average particle size of 1.2 μm (Spharosil, from Transparent Materials), 0.80 g of the pyrogenic silica OX-50 (from Evonik), 2.51 g YbF$_3$ (ytterbium trifluoride, average particle size of 0.2 m, from Auer Remy) as well as 2.81 g rheology modifier (InTen-S-Bentone).

After the composites had been prepared, test pieces were prepared, which were irradiated twice for 3 minutes with a dental light source (Spectramat®, Ivoclar Vivadent AG) and thus cured. The flexural strength (FS) and the flexural modulus of elasticity (FM) were determined in accordance with ISO Standard ISO-4049 (Dentistry—Polymer-based filling, restorative and luting materials). For the determination of the polymerization shrinkage force (PSS), the specimens were fixed onto one side of a silanized slide and connected to a Zwick universal testing machine by means of a steel stamp (d=10 mm) treated with bonding agent (Monobond, from Ivoclar Vivadent AG). After setting the layer thickness (0.8 mm) and removing excesses, the measurement was started. The exposure (Bluephase 20i, High Power, 10 s) is effected through the slide and starts 120 s after the start of the measurement. The change in force at a constantly maintained traverse position was recorded over 10 minutes in total. The resulting measured values are collated in Table 1.

The results prove that the composites with urethane allyl compounds according to the invention, i.e. composites K-2 to K-4 and K-6, are characterized by a significantly reduced polymerization shrinkage force compared with reference composite K-5 (without allyl sulfide) and have comparable mechanical properties. In contrast, although composite K-1 based on the allyl sulfide 8 known from the state of the art exhibits a significantly reduced polymerization shrinkage force, the flexural strength and the flexural modulus of elasticity are significantly reduced. Astonishingly, the known allyl sulfide V-783 brings about only a relatively small improvement in the polymerization shrinkage force in comparison with the structurally similar allyl sulfide 6.

TABLE 1

Properties of composites K-1 to K-7

|  | K-1*) | K-2 | K-3 | K-4 | K-5*) | K-6 | K-7*) |
| --- | --- | --- | --- | --- | --- | --- | --- |
| Allyl sulfide | 8 | 3 | 2 | 6 | — | 5 | V-783 |
| FS (MPa) 24 h | 80.7 | 106.0 | 107.8 | 101.8 | 119.7 | 107.2 | 114.7 |
| FS (MPa) 24 h WS$^{1)}$ | 88.0 | 130.9 | 115.3 | 121.4 | 132.3 | 121.9 | 115.3 |
| FM (GPa) 24 h | 3.73 | 5.20 | 5.87 | 4.92 | 6.26 | 6.06 | 7.03 |
| FM (GPa) 24 h WS$^{1)}$ | 3.90 | 6.87 | 6.61 | 6.34 | 7.14 | 7.13 | 7.16 |
| PSS (N) after 125 s | 7.0 | 13.8 | 16.1 | 10.1 | 39.8 | 10.2 | 27.7 |
| PSS (N) after 600 s | 39.4 | 50.5 | 48.5 | 40.9 | 62.8 | 38.8 | 60.2 |

*)Comparison example $^{1)}$WS = Water storage of the test pieces

The invention claimed is:

1. A radically polymerizable dental material, which comprises at least one compound of Formulae I to III:

Formula I $$\left(R^1-O-\underset{O}{\underset{\|}{C}}-C(=CH_2)-CH_2-S-X^1-O-\underset{O}{\underset{\|}{C}}-NH\right)_n-X^2-Y-R^2$$

Formula II $$R^1-O-\underset{O}{\underset{\|}{C}}-C(=CH_2)-CH_2-S-X^1-Z-X^3\begin{array}{c}-O-CO-NH-R^3\\-O-CO-NH-R^3\end{array}$$

Formula III $$R^1-O-\underset{O}{\underset{\|}{C}}-C(=CH_2)-CH_2-S-X^1-O-\underset{O}{\underset{\|}{C}}-NH-X^4-Y-W-Y-X^4-NH-\underset{O}{\underset{\|}{C}}-O-X^1-S-CH_2-C(=CH_2)-\underset{O}{\underset{\|}{C}}-O-R^1$$

in which the variables have the following meanings:

$R^1$ hydrogen, an aliphatic linear or branched $C_1$-$C_{15}$ alkyl radical, which can be interrupted by one or more O or S and which can be substituted or unsubstituted, benzyl or phenyl;

$R^2$ hydrogen, an aliphatic linear or branched $C_1$-$C_{15}$ alkyl radical, which can be interrupted by one or more O or S and which can be substituted or unsubstituted, benzyl, an aromatic $C_6$-$C_{18}$ radical, which can be substituted or unsubstituted, or a (meth)acryloyloxy group;

$R^3$ an aliphatic linear or branched $C_1$-$C_{15}$ alkyl radical, which can be interrupted by one or more O and which can be substituted or unsubstituted, benzyl, or an aromatic $C_6$-$C_{18}$ radical, which can be substituted or unsubstituted;

$X^1$ a linear or branched aliphatic $C_1$-$C_{15}$ alkylene radical, which can be interrupted by one or more O or S, or a cycloaliphatic $C_6$-$C_{16}$ radical;

$X^2$ an (n+1)-valent organic $C_1$-$C_{20}$ radical, which can be interrupted by one or more O or S, a cycloaliphatic $C_5$-$C_{20}$ radical, an aromatic $C_6$-$C_{20}$ radical or an isocyanuric acid radical according to the following formula:

$$\text{isocyanuric ring with } (CH_2)_m \text{ substituents}$$

$X^3$ a 3-valent linear or branched aliphatic $C_3$-$C_{20}$ radical;

$X^4$ a 2-valent organic $C_2$-$C_{30}$ radical, which can be substituted by one or more methyl groups or is unsubstituted;

Y is absent or an ether (—O—), ester (—COO— or —OOC—), urethane (—NR$^4$—CO—O— or —O—CO—NR$^4$—) or amide group (—CONR$^4$— or —NR$^4$—CO—), wherein R$^4$ in each case represents H or a $C_1$-$C_3$ alkyl radical;

Z is absent or an ether (—O—), ester (—COO— or —OOC—), or amide group (—CONR$^5$— or —NR$^5$—CO—), wherein R$^5$ represents H or a $C_1$-$C_3$ alkyl radical;

W an oligomeric polyester, polyether or polythioether group;

m 1, 2, 3, 4, 5 or 6;

n 1, 2, 3 or 4, wherein, if $X^2$ is an isocyanuric acid radical, then Y and $R^2$ are absent and n is 3.

2. The dental material according to claim 1, which comprises at least one additional radically polymerizable monomer and at least one initiator for the radical polymerization.

3. The dental material according to claim 1, wherein the variables have the following meanings:

$R^1$ hydrogen, an aliphatic linear or branched $C_1$-$C_{10}$ alkyl radical, which can be interrupted by one or more O and which can carry one or more substituents, which are selected from —CH$_3$, —C$_2$H$_5$ and/or polymerizable (meth)acryloyloxy groups, or is unsubstituted, benzyl or phenyl;

$R^2$ hydrogen, an aliphatic linear or branched $C_1$-$C_{10}$ alkyl radical, which can be interrupted by one or more O and which can carry one or more substituents, which are selected from —CH$_3$, —C$_2$H$_5$ and/or polymerizable (meth)acryloyloxy groups, or is unsubstituted, benzyl, or an aromatic $C_6$-$C_{12}$ radical, which can carry one or more substituents, which are selected from —CH$_3$, —C$_2$H$_5$, and/or polymerizable (meth)acryloyloxy groups, or is unsubstituted, or a (meth)acryloyloxy group;

$R^3$ an aliphatic linear or branched $C_1$-$C_{10}$ alkyl radical, which can carry one or more substituents, which are selected from —CH$_3$, —C$_2$H$_5$, halogen and/or polymerizable (meth)acryloyloxy groups, or is unsubstituted, benzyl, or an aromatic $C_6$-$C_{18}$ radical, which can carry one or more substituents, which are selected from —CH$_3$, —C$_2$H$_5$, polymerizable vinyl and/or (meth)acryloyloxy groups, or is unsubstituted;

$X^1$ a linear or branched aliphatic $C_1$-$C_{10}$ alkylene radical, which can be interrupted by one or more O, or a cycloaliphatic $C_6$-$C_{12}$ radical;

$X^2$ an (n+1)-valent organic $C_1$-$C_{15}$ radical, which can be interrupted by one or more O, a cycloaliphatic radical or an aromatic $C_6$-$C_{14}$ radical;

$X^3$ a 3-valent linear or branched aliphatic $C_3$-$C_{10}$ radical;

$X^4$ a 2-valent organic $C_2$-$C_{20}$ radical, a cycloaliphatic $C_5$-$C_{10}$ radical or a combination thereof, which can carry one or more methyl groups as substituents, or is unsubstituted;

Y is absent or an ester or urethane group;

Z is absent or an ether or ester group;

W an oligomeric polyester or polyether group and n 1, 2 or 3.

4. The dental material according to claim 3, wherein variables have the following meanings:

$R^1$ an aliphatic linear or branched $C_1$-$C_4$ alkyl radical or benzyl (Ph-CH$_2$—);

$R^2$ hydrogen or a (meth)acryloyloxy group;

R³ a linear $C_1$-$C_3$ alkyl radical, benzyl (Ph-$CH_2$—), phenyl (Ph-) or p-tolyl ($H_3$C-Ph-), wherein these radicals can be substituted in each case by a (meth)acryloyloxy group;

X¹ a linear $C_1$-$C_3$ alkylene radical;

X² an (n+1)-valent linear or branched aliphatic $C_2$-$C_{12}$ radical, which can be interrupted by 1 to 3O, or an aromatic $C_6$-$C_{12}$ radical;

X³ a 3-valent linear or branched aliphatic $C_3$-$C_4$ radical;

X⁴ a 2-valent aliphatic $C_2$-$C_{10}$ radical or a cycloaliphatic $C_6$ radical, which can be substituted with 1 to 3 methyl groups;

Y is absent or an ester or urethane group;

Z is absent;

W an oligomeric polyester or polyether group and n 1, 2 or 3.

5. The dental material according to claim 1, wherein the substituents present in the case of the individual radicals are selected in each case from $C_1$-$C_3$ alkyl groups, halogen, OH, $OCH_3$ or —O—$COCH_3$, polymerizable vinyl, (meth)acryloyloxy and/or (meth)acrylamide groups.

6. The dental material according to claim 1, which contains at least one multifunctional (meth)acrylate or a mixture of mono- and multifunctional (meth)acrylates.

7. The dental material according to claim 1, which comprises at least one filler.

8. The dental material according to claim 1, which additionally comprises at least one photoinitiator for the radical polymerization.

9. The dental material according to claim 1, which comprises
(a) 0.1 to 30 wt.-% of at least one compound of general formula I, II or III,
(b) 5 to 99.1 wt.-% of at least one further radically polymerizable monomer,
(c) 0.01 to 5.0 wt.-% of at least one initiator for the radical polymerization,
(d) 0 to 90 wt.-% of at least one filler, and
(e) 0 to 70 wt.-% of one or more additives,
in each case relative to the total mass of the dental material.

10. The dental material according to claim 9, which has the following composition:
(a) 0.1 to 20 wt.-% of at least one urethane allyl sulfide of general formula I, II and/or III,
(b) 5 to 50 wt.-% of at least one further radically polymerizable monomer,
(c) 0.01 to 5.0 wt.-% of at least one initiator for the radical polymerization,
(d) 10 to 70 wt.-% of at least one filler and
(e) 0 to 5 wt.-% of one or more additives,
in each case relative to the total mass of the dental material.

11. The dental material according to claim 9, which has the following composition:
(a) 0.1 to 20 wt.-% of at least one urethane allyl sulfide of general formula I, II and/or III,
(b) 10 to 50 wt.-% of at least one further radically polymerizable monomer,
(c) 0.01 to 5.0 wt.-% of at least one initiator for the radical polymerization,
(d) 10 to 85 wt.-% of at least one filler and
(e) 0 to 5 wt.-% of one or more additives,
in each case relative to the total mass of the dental material.

12. The dental material according to claim 1, which, apart from one or more compounds of Formulae I, II and III, comprises no volatile mercaptans.

13. The dental material according to claim 1 for intraoral use for the restoration of damaged teeth.

14. The dental material according to claim 1, wherein the variables have the following meanings:

R¹ hydrogen, an aliphatic linear or branched $C_1$-$C_{10}$ alkyl radical, which can be interrupted by one or two O and which can carry 1 to 3 substituents, which are selected from —$CH_3$, —$C_2H_5$ and/or polymerizable (meth)acryloyloxy groups, or is unsubstituted, benzyl or phenyl;

R² hydrogen, an aliphatic linear or branched $C_1$-$C_{10}$ alkyl radical, which can be interrupted by one or two O and which can carry 1 to 3 substituents, which are selected from —$CH_3$, —$C_2H_5$ and/or polymerizable (meth)acryloyloxy groups, or is unsubstituted, benzyl, or an aromatic $C_6$-$C_{12}$ radical, which can carry 1 to 3 substituents, which are selected from —$CH_3$, —$C_2H_5$, and/or polymerizable (meth)acryloyloxy groups, or is unsubstituted, or a (meth)acryloyloxy group;

R³ an aliphatic linear or branched $C_1$-$C_{10}$ alkyl radical, which can carry 1 to 3 substituents, which are selected from —$CH_3$, —$C_2H_5$, halogen and/or polymerizable (meth)acryloyloxy groups, or is unsubstituted, benzyl, or an aromatic $C_6$-$C_{18}$ radical, which can carry 1 to 3 substituents, which are selected from —$CH_3$, —$C_2H_5$, polymerizable vinyl and/or (meth)acryloyloxy groups, or is unsubstituted;

X¹ a linear or branched aliphatic $C_1$-$C_{10}$ alkylene radical, which can be interrupted by one or two 0, or a cycloaliphatic $C_6$-$C_{12}$ radical;

X² an (n+1)-valent an aliphatic $C_1$-$C_{15}$ radical, which can be interrupted by one or two 0, a cycloaliphatic radical or an aromatic $C_6$-$C_{14}$ radical;

X³ a 3-valent linear or branched aliphatic $C_3$-$C_{10}$ radical;

X⁴ a 2-valent aliphatic $C_2$-$C_{20}$ radical, a cycloaliphatic $C_5$-$C_{10}$ radical or a combination thereof, which can carry one or two methyl groups as substituents, or is unsubstituted;

Y is absent or an ester or urethane group;

Z is absent or an ether or ester group;

W an oligomeric polyester or polyether group and n 1, 2 or 3.

15. The dental material according to claim 3, wherein the variables have the following meanings:

R¹ methyl or ethyl;

R² hydrogen or a (meth)acryloyloxy group;

R³ a linear $C_1$-$C_3$ alkyl radical, benzyl (Ph-$CH_2$—), phenyl (Ph-) or p-tolyl ($H_3$C-Ph-), wherein these radicals can be substituted in each case by a (meth)acryloyloxy group;

X¹ a linear $C_1$-$C_3$ alkylene radical;

X² an (n+1)-valent linear or branched aliphatic $C_2$-$C_{12}$ radical, which can be interrupted by 1 to 3O, or an aromatic $C_6$-$C_{12}$ radical;

X³ —$CH_2$—CH (–)—$CH_2$—;

X⁴ a 2-valent aliphatic $C_2$-$C_{10}$ radical or a cycloaliphatic $C_6$ radical, which can be substituted with 1 to 3 methyl groups;

Y is absent or an ester or urethane group;

Z is absent;

W an oligomeric polyester or polyether group and n 1 or 2.

16. The dental material according to claim 1, which comprises
(a) 0.5 to 20 wt.-% of at least one compound of general formula I,
(b) 15 to 95 wt.-% of at least one multifunctional (meth)acrylate,
(c) 0.1 to 3.0 wt.-% of at least one initiator for the radical polymerization,
(d) 0 to 82 wt.-% of at least one filler, and
(e) 0.1 to 60 wt.-% of one or more additives,
in each case relative to the total mass of the dental material.

17. The dental material according to claim 9, which has the following composition:
(a) 0.5 to 10 wt.-% of at least one urethane allyl sulfide of general formula I,
(b) 20 to 40 wt.-% of at least one further radically polymerizable monomer,
(c) 0.2 to 3.0 wt.-% of at least one initiator for the radical polymerization,
(d) 30 to 70 wt.-% of at least one filler and
(e) 0.2 to 4.0 wt.-% of one or more additives,
in each case relative to the total mass of the dental material.

18. The dental material according to claim 9, which has the following composition:
(a) 0.5 to 8 wt.-% of at least one urethane allyl sulfide of general formula I,
(b) 15 to 30 wt.-% of at least one further radically polymerizable monomer,
(c) 0.1 to 0.3 wt.-% of at least one initiator for the radical polymerization,
(d) 30 to 85 wt.-% of at least one filler and
(e) 0.2 to 3.0 wt.-% of one or more additives,
in each case relative to the total mass of the dental material.

19. A method of using a dental material comprising extraorally producing a dental restoration or repairing a dental restoration with the dental material of claim 1.

20. The method according to claim 14, wherein the dental restoration is selected from the group consisting of dental cement, filling composite, inlay, onlay, crown, bridge, dental prosthesis, artificial teeth, and veneering material.

21. A method of using a dental material comprising producing a curable dental material comprising a compound of Formula I, II or III, in which the variables are as defined in claim 1; and
thermally curing and/or light-curing the curable dental material, thereby reducing the polymerization shrinkage stress (PSS) of the dental material.

22. A method of producing a dental material comprising the steps of mixing a compound of Formula I, II or III, in which the variables are as defined in claim 1 with one or more of a radically polymerizable monomer, one or more initiator for the polymerization, one or more filler, and optionally one or more additives; and
thermally curing and/or light-curing the above obtained mixture.

* * * * *